(12) United States Patent
O'Brien et al.

(10) Patent No.: US 11,033,418 B2
(45) Date of Patent: Jun. 15, 2021

(54) BODY SIDE MEMBER OF AN OSTOMY APPLIANCE

(71) Applicant: Coloplast A/S, Humlebaek (DK)

(72) Inventors: Liam O'Brien, London (GB); Philip Holler Langhorn, Hilleroed (DK)

(73) Assignee: Coloplast A/S, Humlebaek (DK)

( * ) Notice: Subject to any disclaimer, the term of this patent is extended or adjusted under 35 U.S.C. 154(b) by 510 days.

(21) Appl. No.: 15/766,368

(22) PCT Filed: Oct. 7, 2016

(86) PCT No.: PCT/DK2016/050325
§ 371 (c)(1),
(2) Date: Apr. 6, 2018

(87) PCT Pub. No.: WO2017/059868
PCT Pub. Date: Apr. 13, 2017

(65) Prior Publication Data
US 2018/0296384 A1    Oct. 18, 2018

(30) Foreign Application Priority Data

Oct. 8, 2015    (DK) .......................... PA 2015 70636

(51) Int. Cl.
*A61F 5/445*    (2006.01)
*A61F 5/44*    (2006.01)
*A61F 5/443*    (2006.01)

(52) U.S. Cl.
CPC ............ *A61F 5/443* (2013.01); *A61F 5/4404* (2013.01); *A61F 5/445* (2013.01)

(58) Field of Classification Search
CPC combination set(s) only.
See application file for complete search history.

(56) References Cited

U.S. PATENT DOCUMENTS

| 5,486,158 | A | * | 1/1996 | Samuelsen | A61F 13/0213 |
| | | | | | 602/46 |
| 5,496,296 | A | * | 3/1996 | Holmberg | A61F 5/443 |
| | | | | | 604/336 |
| 6,312,415 | B1 | * | 11/2001 | Nielsen | A61F 5/443 |
| | | | | | 604/327 |
| 6,863,663 | B1 | * | 3/2005 | Mills | A61F 5/443 |
| | | | | | 604/337 |
| 7,172,581 | B2 | | 2/2007 | Ciok et al. | |
| 2002/0120032 | A1 | * | 8/2002 | Gothjaelpsen | A61F 5/443 |
| | | | | | 523/111 |
| 2003/0004477 | A1 | * | 1/2003 | Nielsen | A61F 5/448 |
| | | | | | 604/336 |
| 2003/0153883 | A1 | | 8/2003 | Hansen et al. | |

(Continued)

FOREIGN PATENT DOCUMENTS

CN    1427702 A    7/2003
CN    101687060 A    3/2010
(Continued)

*Primary Examiner* — Guy K Townsend
(74) *Attorney, Agent, or Firm* — Coloplast Corp., Coloplast A/S; Nick Baumann

(57) ABSTRACT

A body side member of an ostomy appliance having backing film forming a distal surface, the distal surface including one or more individual pockets containing a moldable material that can exit the pockets.

30 Claims, 5 Drawing Sheets

(56) References Cited

U.S. PATENT DOCUMENTS

| | | | |
|---|---|---|---|
| 2004/0260256 A1* | 12/2004 | Ciok | A61F 5/445 604/332 |
| 2007/0249981 A1* | 10/2007 | Hurwitz | A61F 13/0203 602/58 |
| 2009/0148661 A1* | 6/2009 | Stroebech | A61F 5/443 428/137 |
| 2010/0113999 A1 | 5/2010 | Lam et al. | |
| 2010/0114044 A1* | 5/2010 | Cramer | A61F 5/443 604/332 |
| 2010/0324511 A1* | 12/2010 | Dove | A61F 5/445 604/342 |
| 2011/0213322 A1* | 9/2011 | Cramer | A61F 5/443 604/344 |
| 2012/0041404 A1* | 2/2012 | Bach | A61F 5/443 604/344 |
| 2012/0283678 A1* | 11/2012 | Nguyen-DeMary | A61F 5/441 604/337 |
| 2013/0060184 A1* | 3/2013 | Rea | A61F 13/0246 602/54 |
| 2013/0123678 A1* | 5/2013 | Carty | A61F 13/0253 602/54 |
| 2013/0138065 A1 | 5/2013 | Buus | |
| 2013/0226116 A1* | 8/2013 | Edvardsen | A61F 5/445 604/338 |
| 2013/0226117 A1* | 8/2013 | Hansen | A61L 24/046 604/338 |
| 2014/0128825 A1 | 5/2014 | Klein et al. | |
| 2018/0289527 A1* | 10/2018 | Vila | A61F 5/445 |
| 2018/0296384 A1* | 10/2018 | O'Brien | A61F 5/443 |
| 2020/0015996 A1* | 1/2020 | Schertiger | A61F 5/4401 |
| 2020/0046541 A1* | 2/2020 | Sund | A61F 5/443 |

FOREIGN PATENT DOCUMENTS

| | | |
|---|---|---|
| CN | 102883691 A | 1/2013 |
| CN | 103068347 A | 4/2013 |
| CN | 103561693 A | 2/2014 |
| CN | 103561695 A | 2/2014 |
| DE | 3376385 D1 | 6/1988 |
| EP | 0686381 A1 | 12/1995 |
| EP | 0882437 A2 | 12/1998 |
| EP | 0991382 A1 | 4/2000 |
| RE | 0089138 A2 | 9/1983 |
| RU | 2008151158 A | 6/2010 |
| RU | 2011147047 A | 5/2013 |
| WO | 9855057 A1 | 12/1998 |
| WO | 03061720 A1 | 7/2003 |

\* cited by examiner

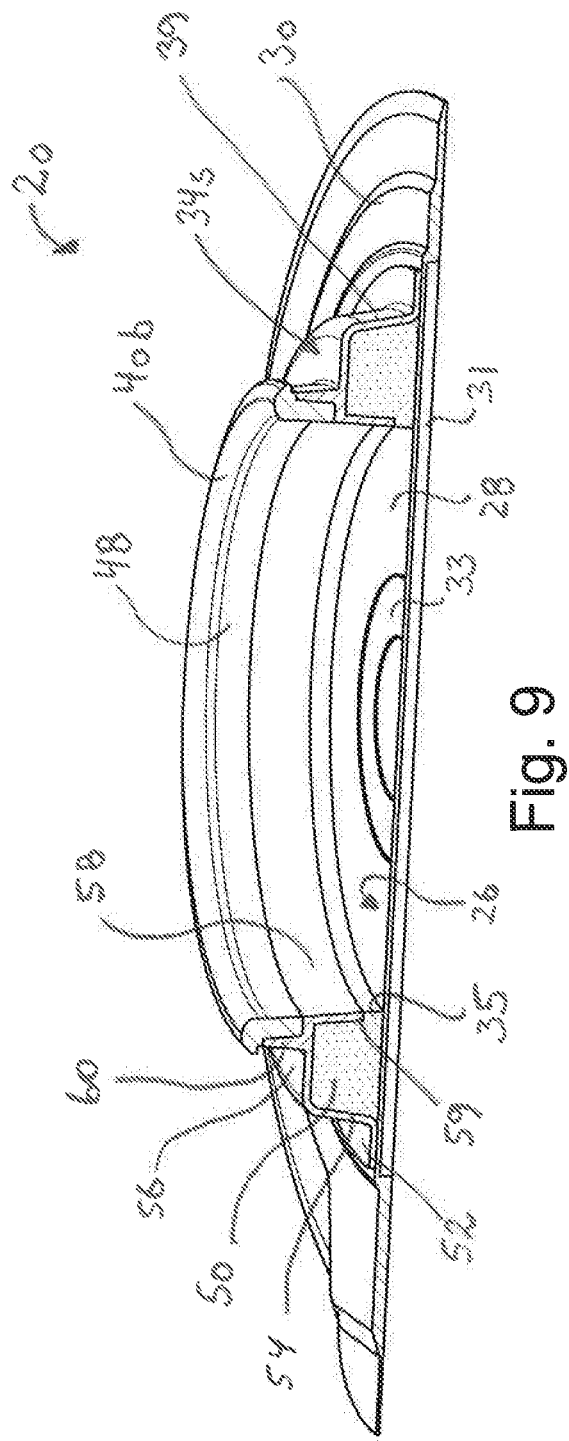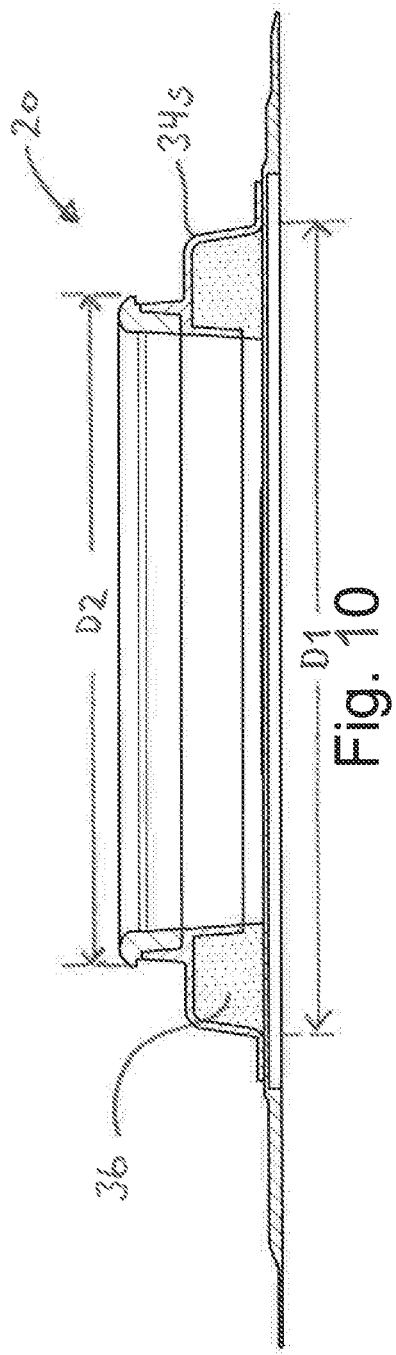

BODY SIDE MEMBER OF AN OSTOMY APPLIANCE

SUMMARY

The present disclosure provides aspects of a body side member of an ostomy appliance according to the appended claims.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 9 is a schematic, perspective cross-sectional view of one embodiment of a body side member of an ostomy appliance.

FIG. 10 is a cross-sectional view of one embodiment of a body side member of an ostomy appliance.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus the axial direction is generally perpendicular to the abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner".

Figure 1:
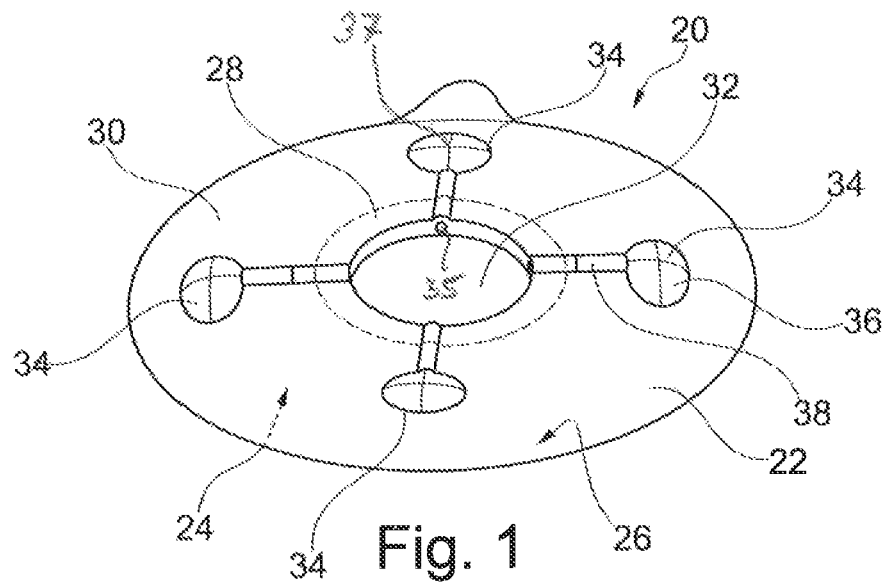
FIG. 1 is a schematic, perspective view of one embodiment of a body side member of an ostomy appliance.
Figure 3:
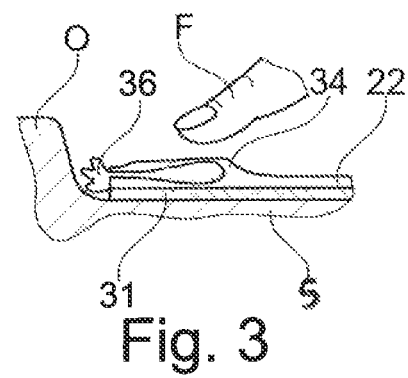
FIG. 3 is a schematic sectional view of one embodiment illustrating a portion of a body side member.

FIG. 1 is a schematic, perspective view of one embodiment of a body side member 20 of an ostomy (or stoma) appliance. The body side member 20 includes a backing film 22 having a proximal surface 24 ("underside" in FIG. 1) and a distal surface 26 ("overside" in FIG. 1). The backing film 22 is defined by a first zone 28 and a second zone 30 surrounding the first zone 28. The proximal surface 24 of the backing film 22 comprises an adhesive 31 (FIG. 3). In embodiments, the adhesive 31 comprises a plurality of different adhesive materials. In one embodiment, the different adhesive materials of the adhesive 31 are provided in a side-by-side manner. In one embodiment, the different adhesive materials of the adhesive 31 are provided in a layered structure. In one embodiment, the different adhesive materials of the adhesive 31 are provided primarily side-by-side, but with some overlapping portions of the different adhesive materials.

In embodiments, the body side member 20 includes a stoma-receiving opening 32 extending through the backing film 22 and the adhesive 31. In embodiments, stoma-receiving opening 32 is surrounded by the first zone 28. In embodiments, the distal surface 26 of the backing film 22 is configured to have a plurality of pockets 34 containing a moldable material 36. A plurality should be interpreted as two or more individual pockets. In embodiments, the moldable material 36 is adapted to be dispensable from each individual pocket 34 when the body side member 20 is in use on a skin surface S around a stoma O of a user (see FIG. 3). Stated differently, in one embodiment of the body side member 20, the dispensing of moldable material 36 from one of the pockets 34 can be done independently of the dispensing of moldable material 36 from any one or more of the other pockets.

Figure 2:
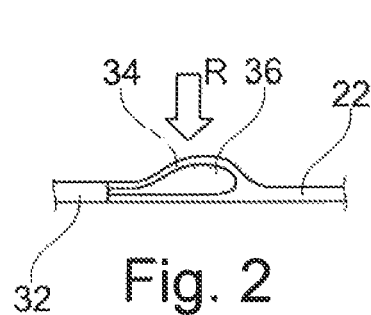
FIG. 2 is a schematic sectional view of one embodiment showing a body side member comprising moldable material.

FIG. 2 is a schematic sectional view of one embodiment showing an a pocket 34 containing moldable material 36. By applying finger pressure to an outer or exterior (distal)

surface of the pocket 34, indicated by arrow R, the moldable material 36 is dispensable from the pocket 34.

FIG. 3 is a schematic sectional view of one embodiment illustrating a portion of the body side member 20 in place on the skin surface S around a stoma O of a user. The backing film 22 is adhered to a peristomal area of the skin surface S by the adhesive 31. A finger F of a user is shown to provide pressure to the pocket 34 to dispense in an active manner the moldable material 36 from the pocket 34 to engage with the stoma's surface. FIG. 3 illustrates one embodiment wherein the pocket 34 has a reduced axial protrusion from the distal surface 26 after some dispensing of moldable material 36. In embodiments, the moldable material 36 provides an adhesive mass that can adapt closely to the surface shape of the stoma O, thereby providing for an improved sealing effect against stomal output coming into contact with the adhesive 31.

Figure 4:
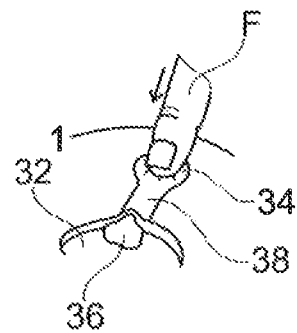
FIG. 4 is a perspective sectional view of one embodiment illustrating a situation similar to the situation in FIG. 3.

FIG. 4 is a perspective sectional view of one embodiment illustrating a situation similar to the situation in FIG. 3, but not showing the stoma O to better illustrate the moldable material 36 being dispensed into the stoma-receiving opening 32 to seal against the stoma O.

In one embodiment, each pocket 34 is connected to and in communication with a channel 38 extending from the pocket 34 towards the stoma-receiving opening 32 of the backing film 22. Exemplary embodiments of a channel 38 are illustrated in FIGS. 1 and 4. In one embodiment, the channel 38 extends in a generally radial direction of the body side member 20 from the pocket 34 towards a central longitudinal axis extending through the stoma-receiving opening 32. Embodiments of the body side member 20 including a channel 38 between a pocket 34 and the stoma-receiving opening 32 provide for the moldable material 36 to be stored at a distance from the stoma-receiving opening 32. This in turn allows the user to customize, such as by cutting with a scissors, the stoma-receiving opening 32 to his/her particular stoma size before application of the moldable material 36 without having to perform the cutting in the moldable material 36, which in some implementations can be relatively soft and sticky and thus difficult to cut properly. When the body side member 20 has been applied to the skin surface S around the stoma O, the moldable material 36 can subsequently be dispensed from the pocket 34 out into the stoma-receiving opening 32 and adapt to the small folds and creases of the stoma surface, thereby creating an improved seal.

In one embodiment, the pocket 34 is in direct communication with the stoma-receiving opening 32 of the backing film 22. This provides for finger pressure applied to each individual envelope 34 to cause dispensing of moldable material 36 into the area surrounding the stoma O, and that no intermediate portions or reservoirs and/or pathways for the adhesive material 36 to travel in from the pocket 34 to the stoma-receiving opening 32 are present. Stated otherwise, in embodiments there is no channel or canal present between the pocket and the stoma-receiving opening.

Figure 5:
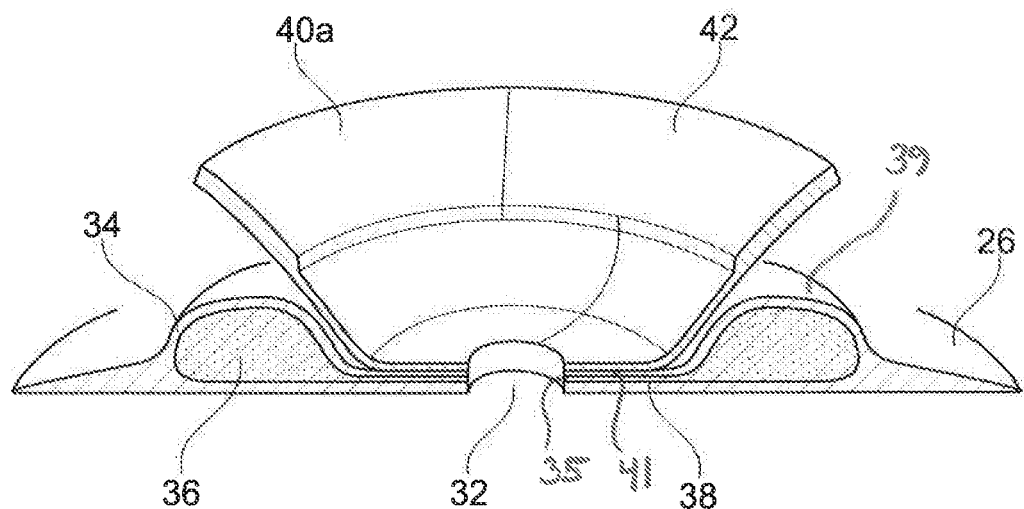
FIGS. 5 and 6 are schematic, cross-sectional views illustrating embodiments of a body side member including coupling interface halves.
Figure 6:
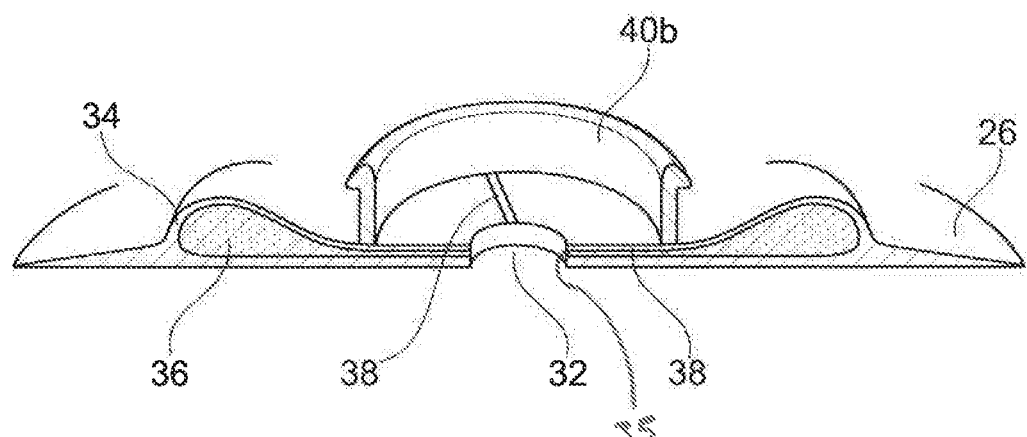
Figure 12:
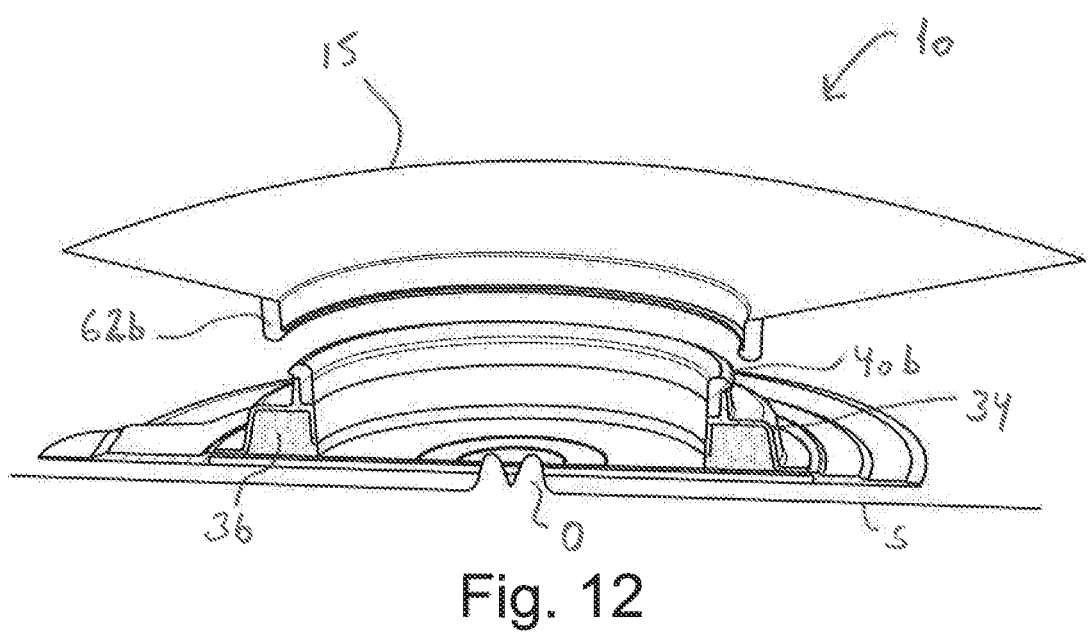
FIG. 12 is a schematic, cross-sectional view of one embodiment of an ostomy appliance.

In embodiments, and illustrated in the schematic, cross-sectional views of FIGS. 5 and 6, the distal surface 26 of the backing film 22 includes a first half 40a, 40b of a coupling interface for coupling the body side member 20 to a stomal output collecting bag (FIG. 12). In one embodiment, the coupling half 40a is a flange adapted to provide a surface 42 for attaching another coupling half in the form of an adhesive flange provided on a stomal output collecting bag. In one embodiment, the coupling half 40b is an annular ring comprising an upstanding flange protruding from the distal surface 26 perpendicular thereto for attaching another coupling half in the form of a coupling ring provided on a stomal output collecting bag. In one embodiment, a first coupling half 40a, 40b is attached to the distal surface 26 of the backing film 22. In embodiments, the first coupling half 40a, 40b is attached to the distal surface 26 by an adhesive or by welding, but other ways of attaching are acceptable. As illustrated by way of example in FIG. 6, in embodiments a first coupling half 40b is attached to the distal surface 26 at a location radially closer to the stoma-receiving opening 32 than where the pocket 34 is located. In embodiments, the channel 38 extends from the pocket 34 under (below) the location of attachment of a first coupling half 40a, 40b.

Figure 7:
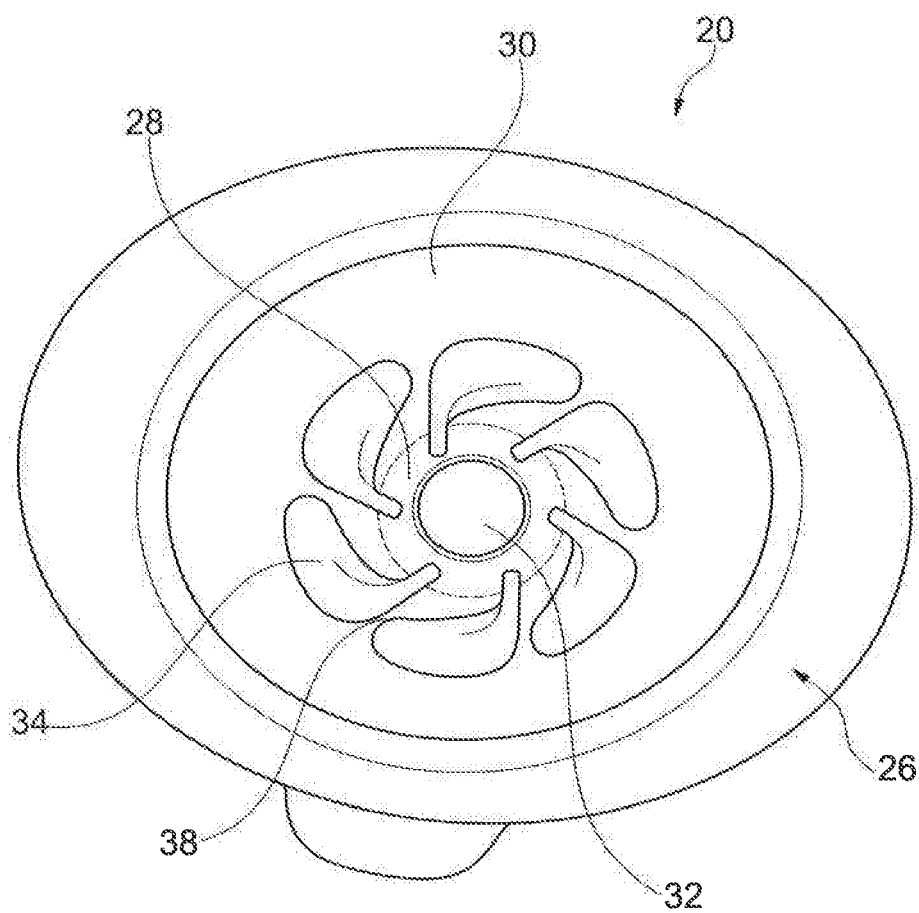
FIG. 7 is a schematic top view showing a distal surface of one embodiment of a body side member.
Figure 8:
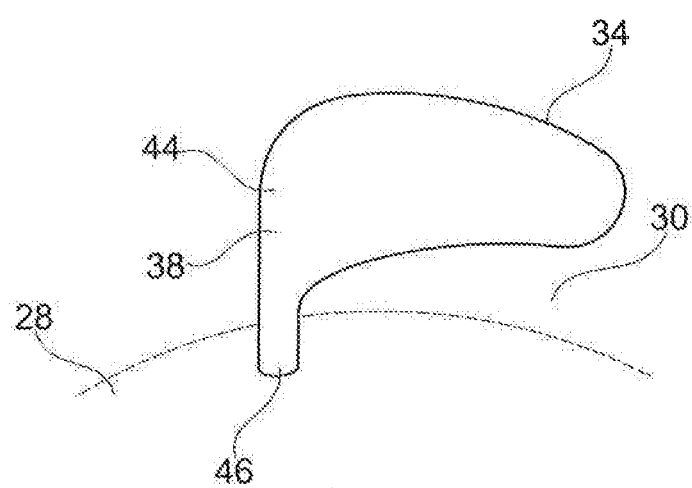
FIG. 8 is an enlarged schematic top view of a single, exemplary pocket according to one embodiment of a body side member.

FIG. 7 is a schematic top view showing the distal surface 26 of one embodiment of the body side member 20 and FIG. 8 is an enlarged schematic top view of a single (individual), exemplary pocket 34 according to one embodiment. In one embodiment, the channel 38 includes a first open end portion 44 in communication with the pocket 34 and a second closed end 46 portion located in the first zone 28 of the backing film 22. In embodiments, the pocket 34 is located in the second zone 30 with the channel 38 extending from the pocket 34 in the second zone 30 into the first zone 28. In one embodiment, each individual pocket 34 is located in the second zone 30 of the backing film 22.

In one embodiment, the body side member 20 includes four individual pockets 34. In one embodiment, the body side member 20 includes six individual pockets 34.

In one exemplary implementation and application of the body side member 20 according to the present disclosure, a user initially customizes, such as by cutting, a stoma-receiving opening 32 to an approximate size or circumference of the user's individual stoma O. By cutting the stoma-receiving opening 32, which will be located in the first zone 28 of the backing film, the user simultaneously cuts off or open the closed end portions 46 of the channels 38 leading from the individual pockets 34. This creates communication for the moldable material 36 located in the pocket and the stoma-receiving opening 32. The user then removes any protective liner(s) provided on the adhesive 31 of the proximal surface 24 of the backing film 22 and applies the body side member 20 to the skin surface S around the stoma O. The user then applies finger pressure to each individual pocket 34 to dispense the moldable material 36 from the pocket 34 via the channel 38 out into the stoma-receiving opening 32. Here, the moldable material 36 engages with the stomal surface. In embodiments, the moldable material 36 is configured to undergo a swelling action by absorption of moisture from the stomal output and/or from the mucous membrane of the stoma. In embodiments, the swelling of the moldable material 36 helps to create an improved seal between the stoma O and the body side member 20, thereby reducing the probability of leakage caused by stomal output attacking the adhesive 31. The user repeats the procedure of applying finger pressure for each pocket 34 such that the sealing effect is achieved around the circumference of the stomal surface.

Figure 11:
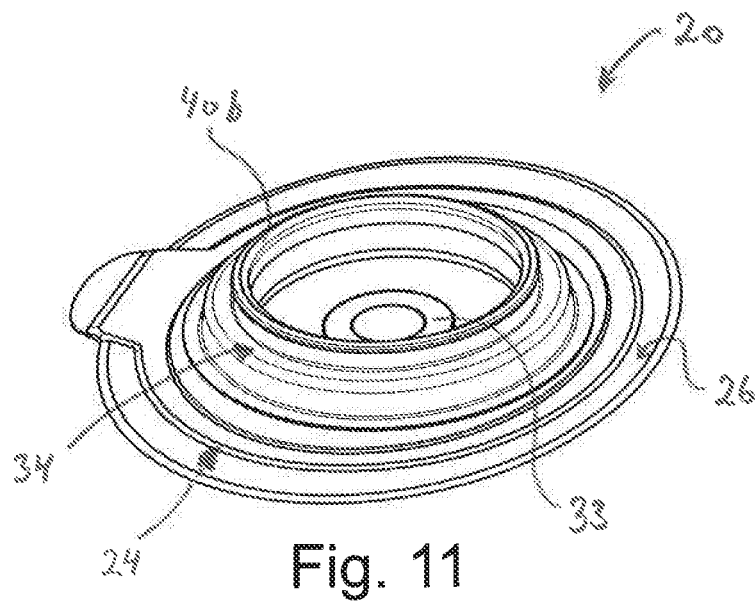
FIG. 11 is a schematic, perspective view of one embodiment of a body side member of an ostomy appliance.

FIGS. 9-11 disclose embodiments of a body side member 20 including a backing film 22 having a proximal surface 24 and a distal surface 26. The backing film 22 has a first zone 28 and a second zone 30 surrounding the first zone, and at least a portion of the proximal surface 24 of the backing film 22 comprises an adhesive 31. Suitable materials for the adhesive 31 on the proximal surface of the backing film include adhesives of the types disclosed in the publications WO2007/082538 and WO2009/006901.

In embodiments, at least a centre portion 33 of the first zone 28 is prepared for provision of a stoma-receiving opening 32 (FIGS. 9 and 11). The stoma-receiving opening 32 extends through the backing film 22 and the adhesive 31. In embodiments, the distal surface 26 of the backing film 22 includes one or more pockets 34 containing a moldable material 36. In embodiments, the moldable material 36 is configured to exit one or more pockets 34 via a pocket opening 35 in use of the body side member 20 on a skin surface S around a stoma O of a user.

Thereby, a body side member 20 is provided that allows for externalization of the moldable material 36 from a pocket 34. Some persons with an ostomy have mild to severe skin surface irregularities in the peristomal area, which makes it difficult to fit a "standard" ostomy appliance to the skin to properly match their individual irregularities. Many will try to compensate for the irregularities by applying one or more accessory products, such as adhesive paste rings or strip pastes to "fill" such irregularities in addition to their primary ostomy appliance. Not only is this an impracticality and often also an economical nuisance to the user. Experience moreover shows that such compensation attempts rarely have any significant effect on the frequency of leakage incidents. In contrast to this, embodiments according to the present disclosure are advantageous in that they provide a body side member 20 of an ostomy appliance that does not require the use of accessory products. Other advantages include that the pockets 34 of the disclosed body side member 20 are not limited to containing a specific kind of moldable material 36. This in turn means that the body side member 20 alternatively or additionally offers solving of other frequently occurring problems with stoma appliances adhered to the skin. Such other problems that the body side member 20 may help to alleviate include, but are not limited to, prevention of disintegration and/or reduction in the loss of adhesive effect between the skin adhesive (comparable to adhesive 31) and the user's skin.

Stomal output exudating from the stoma "mouth" and from the exterior surface of the stoma often contains fluids that are aggressive to the user's skin and to the skin adhesive material.

In some implementations, the body side member 20 according to the present disclosure helps to provide a sealing effect that reduces the frequency of disintegration of the adhesive matrix of the adhesive 31. This is at least partly because of the provision of moldable material 36 that can be externalized from the distal surface 26 of the backing film 22, which may then be brought into contact with the stoma surface to prevent aggressive stomal outputs from entering underneath the adhesive 31.

Other helpful effects are envisioned by the body side member 20 according to the disclosure, some of which effects are believed to be at least partly controllable by the applied number of pockets 34 and by the composition of the moldable material 36. In embodiments, the pocket(s) comprise(s) more than one kind of moldable material 36. In embodiments, different pockets 34 contain different moldable materials 36. Thereby, it is believed that more than one helpful effect can be achieved by the body side member 20. Even further, as an example, in embodiments wherein more than one kind of moldable material 36 is provided in pockets 34 of the body side member 20, the helpful effect(s) presented by one moldable material may be amplified by the presence of another kind of moldable material to provide even better results in terms of reduction or elimination of leakage incidents.

In embodiments, the pocket opening 35 of at least one pocket 34 faces towards the centre portion 33 of the body side member 20. This provides for the pocket opening 35 to face radially inward towards the stoma O when the body side member 20 is in use on the skin surface S of a user. Thereby, any moldable material 36 exiting a pocket 34 is directed immediately in the direction of any stomal output or moisture emanating from the stoma or the stoma surface. Thus, in embodiments, each pocket opening is configured such that it directs moldable material, already swelled or undergoing swelling in response to moisture absorption, in a radial direction towards an axis being perpendicular to the proximal and distal surfaces of the backing film and extending through the centre portion. Thereby, in use, the pocket opening 35 effectively guides the moldable material 36 towards the stoma for alleviation of one or more of the problems discussed in this disclosure.

In embodiments, each pocket opening 35 is located at a portion of the pocket 34 that is radially closest to the centre portion 33 of the body side member 20 and axially closest to the distal surface 26 of the backing film 22

In embodiments, a pocket 34 includes a plurality (two or more) of pockets openings 35 (not shown). This allows for body side members 20 according to the disclosure having a relatively simple structure while simultaneously allowing for moldable material 36 to be externalized from different and/or multiple pocket openings 35, thereby providing for a versatile distribution of the moldable material 36, particularly over the first zone 28 of the body side member 20.

In embodiments, the moldable material 36 is configured to be dispensed from one or more pockets 34. By 'dispensed' is to be understood that in some implementations, in order for the moldable material 36 to exit a pocket 34, the pocket 34 has to be manipulated by a user's fingers. In other words, 'dispensed' should be interpreted to mean that the externalization of moldable material 36 constitutes an action or step that requires active participation or contribution by the user. In embodiments, an exterior surface of a pocket 34 includes a texture 37 for facilitating easier tactile recognition of where to manipulate the pocket 34. The texture 37 is further useful to prevent the user's fingers from slipping off the exterior surface of the pocket 34 during such manipulation.

In use of the body side member 20, and depending on the nature of the moldable material 36, in some embodiments moisture absorption and the resulting swelling of the moldable material 36 initiates the exiting of the moldable material 36 towards the stoma O without any manipulation of the pocket 34 required by the user. In other words, the externalization of the moldable material 36 from a pocket 34 starts "automatically" as soon the moldable material 36 begins to take up moisture. It has been found that the rate of the externalization of the moldable material 36 can be surprisingly high, thereby causing a fast release of the moldable material 36. This is helpful in getting the moldable material 36 towards the stoma as quickly as possible, thereby providing faster and thus better security against leakage incidents. This is further advantageous at least in that does not require any active participation of the user in externalizing the moldable material 36 from a pocket 34.

In embodiments, the one or more pockets 34 is/are attached to the distal surface 26 of the backing film 22. Thereby, each pocket 34 forms an element that is separate from the backing film 22 and is attached as such to the backing film 22. In some implementations, such separate structure of a pocket 34 facilitates the manufacture of the body side member 20 in that the moldable material 36 and the pocket 34 can be produced and prepared in a process independent of producing the other elements of the body side member 20 and/or the stoma appliance. This is advantageous because relevant process parameters for handling the moldable material 36 (e.g. temperature and pressure) and the adhesive 31 can be significantly different from each other. In embodiments, the one or more pockets 34 are formed in the backing film 22. In these implementations, a pocket 34 is formed in the backing layer 22 itself. In other words, a pocket 34 does not form an element that is separate from the backing layer 22. A pocket 34 can thus advantageously have an envelope structure in the distal surface 26 of the backing film 22. Thereby, the body side member 20 with the pockets 34 can be produced with fewer individual materials involved in the manufacturing process.

In embodiments, a wall 39 (FIGS. 5, 11) of the pocket 34 comprises a flexible sheet material. In embodiments, the flexible sheet material of the pocket 34 is identical to the material from which the backing film 22 is made. In other embodiments, the flexible sheet material is a material that is different from the material of the backing film 22. In embodiments (FIG. 5), the wall 39 of the pocket 34 comprises a differentiated thickness when viewed over a total extent of the pocket 34. In one embodiment, a thickness of the wall 39 decreases from a greater thickness at an outer periphery portion of the pocket 34 to be thinner radially closer to the centre portion 33 of the body side member 20. One exemplary implementation of this is shown at reference 41 in FIG. 5. The differentiated thickness of the wall 39 of the pocket 34 is believed to be useful in providing a smooth externalization of the moldable material 36 from the pocket 34, and also for correctly guiding the moldable material 36 radially towards the stoma O in use.

In embodiments, a wall 39 (FIGS. 9-11) of the pocket 34 is formed by a resilient material. In some implementations, such forming of the wall 39 in a resilient material facilitates the externalization of the moldable material 36 from the pocket, particularly in that the resiliency of the material causes the wall 39 to return to its original/initial shape after the exterior surface of the pocket 34 has been manipulated ("squeezed") by a user's fingers. Suitable resilient materials for the wall 39 include, but are not limited to, thermoplastic elastomers (TPE's) and/or mixtures thereof. In embodiments, a wall 39 of the pocket 34 is made in an injection molding process. Alternatively or additionally, the wall 39 is made in a two-component casting process, advantageously in combination with the provision of a first half of a coupling interface (described above).

In embodiments, one or more pockets 34 is/are attached to a first half 40a, 40b of a coupling interface for connection of the body side member to a stomal output collecting bag, one exemplary implementation being shown in FIGS. 5 and 6.

In embodiments, one or more pockets 34 is/are provided distal to the distal surface 26 of the backing film 22 and proximal to a first half 40a, 40b of a coupling interface for connection of the body side member 20 to a stomal output collecting bag. In embodiments, the first half 40a, 40b of the coupling interface is attached to a distal-most portion of one or more pockets 34 (FIGS. 5 and 6).

In the embodiments illustrated in FIGS. 9-12, the distal surface 26 of the backing film 22 has one single pocket 34s. One single pocket should be interpreted to mean one and only one pocket 34s. Among other advantages, this provides for a body side member 20 to be produced involving less complicated production steps.

In embodiments, the single pocket 34s is configured to extend annularly around the centre portion 33 of the body side member 20. Among other advantages, these embodiments are particularly suitable for a relatively simple production process.

In embodiments, the single pocket 34s is attached to a first half 40a, 40b of a coupling interface for connection of the body side member 20 to a stomal output collecting bag. Exemplary implementations of such embodiments are most clearly illustrated in FIGS. 9-11. In embodiments, the first half 40a, 40b of the coupling interface can advantageously be produced by a two-component casting process providing a combined "pocket/coupling"-element, wherein the material of the pocket 34 is different than the material of the first half 40a, 40b of the coupling interface. As an example, the material of the pocket 34 is resilient, while the material of the coupling half 40a, 40b is stiff and less flexible in comparison.

In the following, particular reference is made to FIGS. 9-11. In embodiments, the first coupling half 40b is configured as an annular ring including an upstanding flange 48 extending axially away from the distal surface 26 of backing film 22 and/or axially away from the single pocket 34s. In one embodiment, the first half 40b of the coupling interface is attached to a distal-most portion of the single pocket 34s. In one embodiment, the single pocket 34s has an outer perimeter that defines a first, outer diameter D1 being greater than a second, maximum outer diameter D2 of the annular ring forming the first half 40b of the coupling interface.

In other embodiments, the first half 40a, 40b of the coupling interface is configured as a flexible, planar annular flange (not shown), optionally comprising an adhesive. The first half 40a, 40b is adapted to couple with a second half provided around an inlet opening of a stomal output collecting bag by means of adhesion. Coupling interfaces of this kind are available on the markets.

In the embodiments of FIGS. 9-11, as best illustrated in the cross-sectional view of FIG. 9, the pocket opening 35 is located immediately above the distal surface 26 of the first zone 28 of the backing film 22. In embodiments, the single pocket 34s includes a reservoir 50 containing a major portion of the moldable material 36. In embodiments, the pocket 34s including the reservoir 50 is defined by a wall 39 of the pocket 34s extending generally in an "S"-shape configuration including a proximal flange 52, a connecting flange 54 and a distal flange 56. In embodiments (not shown), the reservoir 50 is connected to the pocket opening 35 via a canal. In embodiments, the moldable material 36 is configured to be in fluid communication between the reservoir 50 and the pocket opening 35 via the canal. Thereby, the size of the reservoir 50 and/or the externalization characteristics (such as, but not limited to, speed of exiting moldable material 36, finger pressure needed, ejection direction etc.) can be configured according to needs.

In embodiments, a skirt 58 extends towards the distal surface 26 of the backing film 22 from a radially innermost portion of the distal flange 56 (seen in relation to a central axis extending through the centre portion 33).

In embodiments, the pocket opening 35 is defined by a gap between a proximal-most portion 59 of the skirt 58 and the distal surface 26 of the backing film 22. In embodiments, some sections of the proximal-most portion 59 of the skirt 58 extend proximally into contact, or alternatively into attachment, with the distal surface 26 of the backing film 22 while at other sections the gap is present. This provides one option for a body side member 20 having one single pocket 34s comprising a plurality of pocket openings or gates 35. In embodiments, the gates need not be of the same magnitudes/ sizes such as to provide an option for differentiating the exposure to the moldable material 36 of different portions of the first zone 28 of the backing film 22. This can be advantageous in that is allows for users to potentially apply more moldable material 36 in one area around the stoma than in another area around the stoma.

In embodiments, a protrusion 60 extends distally from the distal flange 56. In embodiments, the protrusion 60 provides at least a radial abutment of the pocket 34s against which the annular ring of the first half 40b of the coupling interface abuts.

In embodiments of FIGS. 9-11, only a minor surface portion of the moldable material 36 is exposed at each pocket opening 35. In the figures, this is illustrated by the relatively small amount of moldable material 36 not being confined by the wall/flanges 39, 54, 56, 58 of the single pocket 34s present at the gap of the pocket opening 35. This is advantageous in that it allows for controlling where and how quickly moisture and exudates from the stomal output can "attack" the moldable material 36. In other words, the structure of the pocket 34s in the embodiments of FIGS. 9-11 protects the moldable material 36 from being exposed from more than one side.

Embodiments illustrated in FIGS. 9-11 are further advantageous in that the moldable material 36 will not be immediately visible to the user, thereby providing a visually simpler impression of the ostomy appliance. Moreover, because the moldable material 36 is generally protected in the pocket 34s, the distal surface 26 of the first zone 28 of the backing film 22 can be cleaned (wiping off stomal output and already eroded/used moldable material 36) during an exchange of the stomal output collecting bag (in the case of a two-piece appliance, see below) without inadvertently also removing still viable moldable material 36.

Another advantage of the body side members 20 disclosed herein, is that a user adapting stoma receiving opening 32 of the ostomy appliance before application to the skin, such as by cutting with a pair of scissors, does not have to be concerned with cutting away or removing viable moldable material 36. Applying the pockets 34 in a body side member 20 according to the disclosure ensures that the moldable material from manufacture is provided sufficiently remote from the centre portion 33 prepared for the individual user customization.

In one aspect, the disclosure relates to an ostomy appliance 10 including a body side member 20 as described above and a stomal output collecting bag 15 configured to attached to the distal surface 26 of the backing film 22 of the body side member 20.

In one embodiment, the ostomy appliance 10 is a so-called one-piece ostomy appliance, i.e. without a coupling interface between the body side member 20 and the stomal output collecting bag (not shown). In another embodiment, as most clearly illustrated in FIG. 12, the ostomy appliance 10 is a two-piece appliance including a coupling interface 40b, 62b for connecting a stomal output collecting bag 15 to the body side member 20.

In embodiments, the moldable material 36 includes an adhesive. Suitable materials for the moldable material 36 of the at least one pocket 34 include adhesives, such as, but not limited to, adhesive pastes. Suitable materials for a paste-type adhesive comprises adhesives of the types disclosed in WO2010/069334. Other types of adhesive pastes are also acceptable.

In embodiments, the moldable material 36 includes a moisture absorbing component. In embodiments, the moisture absorbing component has a high absorption capability or potential and in other embodiments, the moisture absorbing component has a small absorption capability. Suitable materials for the moisture absorbing component include, but are not limited to, superabsorbent polymers commonly made from poly-acrylic acid salts.

In some embodiments, the moldable material is an adhesive provided as a composition comprising a polymer and a switch initiator, wherein the composition can be switched from a first liquid state to a second adhesive state by activation of the switch initiator; the composition having in the first liquid state a complex viscosity $|\eta^*|$ below 0.4 MPa s; and having in the second adhesive state a second repeated peel force above 1 N/25 mm.

The present inventors have found that a composition having in the first liquid state a complex viscosity $|\eta^*|$ below 0.4 MPa s is advantageous in that it is capable of quickly flowing into the structure of a substrate, such as skin, and therefore is able to quickly wet the substrate and form a good basis for sufficient adhesion. Wetting means that the composition comes into direct contact with the surface of the substrate, including, where relevant, flowing into the micro and macro structures of the substrate.

In particular, within the field of pressure sensitive adhesives to be used for ostomy devices, our experiments have shown that a complex viscosity of 0.4 MPa s is the upper threshold for when a composition will flow sufficiently fast into the roughness of the skin and hereby obtain a desired adhesive contact in order to be able to seal around the stoma of a user within the period of time actually used by the average ostomy device user to attach the device on the skin.

In embodiments, the activation of the switch initiator is caused by exposure of the switch initiator to moisture. The moisture may be from the natural humidity of the air or it may be specifically provided, e.g., by applying water to the adhesive composition. The moisture used to activate the switch initiator may also, wholly or partly, come from the skin of the user.

Compositions that contain a moisture switchable switch initiator are sometimes referred to as "moisture curing" compositions. This merely means that the switch takes place by exposure to moisture. Moisture curing and moisture switchable are used interchangeably herein.

In some embodiments, the composition comprises a water absorbent material in an amount of 1-60% (w/w) of the composition.

In some embodiments, the water absorbent material is selected from hydrocolloid, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol and mixtures thereof.

In embodiments, the composition comprises a silicone polymer.

Moisture curing materials are polymeric materials that change from a liquid to a solid state when exposed to moisture. When these materials solidify, they are capable of sustaining deforming forces.

Moisture curing materials may comprise several components including a reactive polymer, a catalyst, a viscosity modifier, a crosslinker, and a water scavenger. The function of the reactive polymer together with a catalyst and a crosslinker is to form a polymer network upon exposure to moisture. This event makes moisture curing materials change from a liquid to a solid state. This may be referred to as "switching" or "curing".

The function of a viscosity modifier is to tune the viscosity to fulfill the requirements of each application. The function of the water scavenger is to prevent unintended curing in the container.

Moisture curing materials may be in one part or in two parts. In case of one-part moisture curing materials, all components may be mixed and stored in a single container until use. Curing starts only once the moisture curing material is open and exposed to moisture. On the other hand, in case of two-component systems, reactive components are isolated from each other in different containers during storage, and come into contact only at the time of use. The reactive components are mixed shortly before use. Curing starts as soon as the reactive components are mixed.

The change of properties from liquid to an adhesive state in moisture curing materials is usually based on condensation cure chemistry.

There is a variety of base polymers with different backbone chemistries, which can lead to condensation cure. Silicone polymers may be used in condensation cure compositions. In order to react via condensation cure, silicones may be terminated with hydroxyl groups in both ends. In the presence of a multifunctional silane, which acts both as cross-linker and water scavenger, catalyst and moisture, hydroxyl terminated silicones will cure. The reactivity of silanol groups vary with the number of electron-withdrawing groups substituents on the silicon atom.

The substituents on the multifunctional cross-linker is a relevant parameter, which may affect the cure speed. A trifunctional, tetrafunctional, and even higher functional oligomeric and polymeric cross-linkers can be employed. In embodiments, different substituents, such as methyl, ethyl, and vinyl groups may be used. Examples of trifunctional cross-linkers based on alkoxy groups include methyl trimethoxy silane and methyl triethoxy silane. In addition to alkoxy, acetoxy, oxime, amine, amide, and enoxy cure systems are available.

The curing systems may be adapted to different applications depending on by-products of the curing process. For example, for ostomy care, by-products should be non-toxic and should not have a bad smell.

A suitable condensation cure catalyst is chosen depending on the chemistry of the multifunctional silane. Titanates are employed with alkoxy, amide, or oxime systems, whereas tin catalysts may be added to acetoxy, oxime, and amine cure formulations. In embodiments, the titanate catalyst used is selected from tetraalkoxy titanates and chelated titanates. Tetraalkoxy titanates are the more catalytically active species.

The rate of condensation curing depends on the cross-linking agent (its functionality, concentration, and chemical structure), the type of catalyst, and the relative humidity of the environment.

Moisture curing formulations are interesting materials for applications in ostomy care, either as an accessory or as a full device. Some relevant features to consider for moisture curing compositions to be used in ostomy care:

Safe to use on skin: Moisture curing formulations should be non-toxic before and after cure since they will meet skin.

Adhesion to skin: Moisture curing formulations should adhere to skin before and after cure. Otherwise, these materials will provide a weak interface between the skin and ostomy care device.

Handle moisture from body: Ostomy care products should handle moisture, which comes from skin, output, and sweat. Otherwise, water remaining on the skin weakens the adhesion.

Stable during storage: Moisture curing formulations should be stable during storage in the factory and transportation, but also in the hands of the users before use. Depending on the geographic location, the temperature, and relative humidity of the environment changes. Moisture curing formulations should be stable enough not to cure when exposed to temperatures relevant to storage, transportation, and use situation. In addition, they should be packaged in a way that the moisture cannot diffuse into their container.

Commercially available moisture curing formulations used, e.g., in the construction industry are typically not safe for use on skin. The commercially available "Trio Silken Stoma Gel" from Trio Healthcare is approved for use on skin. However, Trio Silken Stoma Gel has major shortcomings, since it does not adhere to skin and does not absorb body fluids.

Typically, moisture-curing materials for ostomy care applications include a reactive component to cure, a water-absorbing component to absorb moisture from the body, and an adhesive component to enable skin adhesion. A straight-forward strategy to obtain skin adhesives based on moisture curing is to mix unreactive polymers with adhesive character with reactive components, which on their own do not adhere to skin before and after cure. Such materials will be adherent to skin before and after cure. Employing such a strategy opens the opportunity of using a variety of reactive materials available in other industries after necessary modifications to fulfill the bio-safety requirements for skin application. As the water-absorbing component, e.g., natural hydrocolloids or synthetic hydrophilic polymers can be used.

In embodiments, the composition comprises a switch initiator, which is sensitive to moisture. A moisture sensitive switch initiator will cause the composition to switch from a first state, such as a first liquid state, to a second state, such as a second adhesive state, when the moisture sensitive switch initiator is exposed to moisture.

In embodiments, the switch initiator comprises or consists of a moisture sensitive switch initiator. In embodiments, the moisture sensitive switch initiator comprises or consists of a polymer.

In embodiments, the switch initiator comprises or consists of a moisture sensitive silicone polymer, such as Trio Silken (Trio Healthcare).

In general, moisture switchable composition can comprise an unreactive and tacky silicone polymer, such as BIOPSA, and a reactive non-tacky silicon polymer, such as the Trio Silken polymer exemplified herein. In this way, the different functions of crosslinking and tackiness are provided by different polymers, and switching speed and level as well as tack can be adjusted separately. In this manner, switching speed and level can be appropriately modified without compromising tack.

Measurement Methods

Dynamic Mechanical Analysis (DMA) and Determination of Complex Viscosity $|\eta^*|$ The parameter complex viscosity $|\eta^*|$ was measured as follows by a frequency sweep. The adhesives were pressed into a plate of 1 mm thickness. A round sample of 25 mm in diameter was cut out and placed in a Haake RheoStress 6000 rotational rheometer from Thermo Scientific. The geometry applied was parallel plates 25 mm and the shear stress was fixed at 5556 Pa and a gap size of 0.9-1.05 mm was applied to the sample in the beginning of the measurement to obtain a normal force of approximately 5 N. The measurements were carried out at 32° C.

For the complex viscosity |η*| the value measured at a frequency of 0.01 Hz was used. The test was run as a frequency sweep from 100 Hz to 0.01 Hz.

Peel Force

A sample of 25×100 mm was cut from the prepared sheet composition and a 25×300 mm piece of auxiliary tape was then added on the top of the sample. After 30 minutes of conditioning at 23° C. and 50% relative humidity, the sample was mounted in a tensile testing machine (INSTRON 5564 from Instron) and a 90-degree peel test was carried out from a Teflon substrate at a speed of 304 mm/min. The results are given in N/25 mm.

If required for the particular measurement, the samples were switched as described herein below for the individual compositions. The light curing materials that were not to be switched were covered with a light occlusive tape.

Samples were either attached to a substrate and peeled without having been switched at all ("non-switched"), attached to the substrate, then switched, and then peeled ("1$^{st}$ peel, switched on substrate"), attached to a substrate, then switched, then peeled, and then re-attached and peeled a second time ("2$^{nd}$ repeated peel, switched on substrate"), or first switched, then attached to the substrate, and then peeled ("peel when switched off substrate").

For the 2$^{nd}$ repeated peel, switched on substrate, an additional 30 minutes of conditioning at 23° C. and 50% relative humidity was used before performing the second repeated peel.

The peel test was carried out in a climate-controlled room at 23° C. and 50% relative humidity. Peel angle was fixed at 90° and the peel speed was 304 mm/min. Dwell time, meaning the time the sample is rested before testing, was 30 minutes.

The Teflon substrate (2.0 mm PFTE, order no. SPTFE0020INA from RIAS, Roskilde, Denmark) mounted in steel plate was attached to the peel sledge. Adhesive strips were punched out from 0.4 mm thick adhesive sheets in the dimensions 25×100 mm. Auxiliary tape (25 mm width) was mounted on the adhesive with 10 mm overlap. The release liner was lifted in one end to make the overlap with the auxiliary tape. The adhesive was applied to the substrate by using an automatic roll with a load of 2 kg. The average of the mean load was reported as N/25 mm. The failure type, i.e. cohesive or adhesive failure, was observed, recorded, and reported with the peel data.

Moisture Switchable Compositions and Properties

Composition 12: Mixed Moisture-Switchable Silicone Adhesive with 10% Mixed Hydrocolloids Trio Silken (18 g, 36 wt %, Trio Healthcare) was mixed with a mixture of hydrocolloids (5 g, 10 wt %) using Speedmixer at 3000 rpm for 3 minutes. The hydrocolloid mixture consists of carboxymethyl cellulose (20 wt %), guar gum (40 wt %), gelatin (30 wt %) and pectin (10 wt %). An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a polyurethane film (30 μm) using an applicator. For the switch experiments, this composition was switched in either an oven at 32° C., or in a humidity cupboard (Binder KBF) at 32° C. and 50% relative humidity.

Composition 13: Mixed Moisture-Switchable Silicone Adhesive with 10% Potato Starch Trio Silken (18 g, 36 wt %, Trio Healthcare) was mixed with a mixture of potato starch (5 g, 10 wt %) using Speedmixer at 3000 rpm for 3 minutes. An unreactive silicone polymer, BioPSA (27 g, 54 wt %, Dow Corning 7-4560), was added to the mixture, and the mixture was mixed using Speedmixer for additional 3 minutes at 3000 rpm. The resulting mixture was coated on a PU film using an applicator. For the switch experiments, this composition was switched in an oven at 32° C.

Composition 14: Mixed Moisture-Switchable Silicone Adhesive with 10% Carboxymethylcellulose Trio Silken (18 g, 36 wt %, Trio Healthcare) was mixed with a mixture of carboxymethylcellulose (5 g, 10 wt %) using Speedmixer at 3000 rpm for 3 minutes. An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a PU film (30 μm) using an applicator. For the switch experiments, this composition was switched in an oven at 32° C.

| Comp. # | 12 | 13 | 14 |
| --- | --- | --- | --- |
| Polymer type | Silicone | Silicone | Silicone |
| Switch type | Moisture | Moisture | Moisture |
| Absorber amount (w/w) | 10% | 10% | 10% |
| First peel[1] N/25 mm | 3.04 | 3.39 | 2.44 |
| Repeated peel[2] N/25 mm | 3.02 | 3.10 | 2.04 |
| Viscosity[3] Pa s, 0.01 Hz | 351 | 310 | 328 |

[1]Measured after switch on substrate. Adhesive failure mode for all.
[2]Measured after switch on substrate, detachment, and re-attachment. Adhesive failure mode for all.
[3]Viscosity measured before switch.

In another aspect of the disclosure, use of the body side member 20 for an ostomy appliance as disclosed herein for reducing the frequency of stomal output leakage incidents in further contemplated. The advantageous effects provided by the embodiments of the body side member 20, aid in alleviating the nuisances of output leakages often encountered by users of ostomy appliances. This is at least partly achieved by the externalization of the moldable material providing a better security against disintegration of the skin adhesive on the proximal surface of the backing film of the body side member. At the very least, use of the body side member according to the present disclosure allows for an increased wear time of an ostomy appliance.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A body side member of an ostomy appliance, the body side member comprising:
 a backing film comprising a proximal surface and a distal surface, and a first zone and a second zone surrounding the first zone, an adhesive applied to at least a portion of the proximal surface of the backing film, where the adhesive is adapted to secure the ostomy appliance to skin of a user;
a stoma receiving opening formed in the first zone and extending through the backing film and the adhesive;
wherein the backing film further comprises:
a pocket formed between the proximal surface and the distal surface,
a channel located in the first zone and extending from the pocket to the stoma receiving opening; and
a moldable material contained in the pocket;
wherein the channel locates the moldable material contained in the pocket a distance away from the stoma receiving opening such that sizing of the stoma receiving opening by cutting does not cut the moldable material.

2. The body side member of claim 1, wherein the pocket opening is aligned with a centre of the body side member.

3. The body side member of claim 1, further comprising:
a second pocket formed between the proximal surface and the distal surface, with the second pocket separated from and independent from the pocket, and
a second channel located in the first zone and extending from the second pocket to the stoma receiving opening;
wherein the moldable material is dispensable from the second pocket independent from a dispensing of the moldable material from the pocket.

4. The body side member of claim 1, furhter comprising a plurality of individualized and separate pockets, and each of the plurality of individualized and separate pockets contains moldable material that is stored a distance away from the stoma receiving opening.

5. The body side member of claim 1, wherein the moldable material comprises an adhesive.

6. The body side member of any one of claims 1, wherein the moldable material is a moisture absorbing swellable material.

7. The body side member of claim 1, wherein the moldable material is adapted to swell in response to moisture absorption to externalize the moldable material in a radial direction out of the pocket.

8. The body side member of claim 1, wherein the pocket is formed in the backing film.

9. The body side member of claim 1, wherein the pocket is an individual pocket formed by a wall, and the wall is formed as a flexible sheet material on the distal surface of the backing film.

10. The body side member of claim 1, wherein the pocket is adapted to deform in response to an external pressure and return to an original configuration upon removal of the external pressure.

11. The body side member of claim 1, further comprising:
a first coupling interface for connection of the body side member to a stomal output collecting bag;
wherein the pocket is attached to the first coupling interface.

12. The body side member of claim 1, wherein the backing film has one and only one pocket.

13. The body side member of claim 1, wherein the pocket is an annular pocket that extends annularly around the first zone of the backing film.

14. The body side member of claim 1, wherein the pocket is distal to the distal surface of the backing film and proximal to a first coupling interface that is provided for connection of the body side member to stomal output collecting bag.

15. The body side member of claim 1, further comprising a coupling interface:
wherein the coupling interface is attached to a distal-most portion of the pocket.

16. The body side member of claim 1, further comprising a coupling interface:
wherein the coupling interface is an annular ring comprising an upstanding flange extending axially away from the distal surface of the backing film.

17. The body side member of claim 1, further comprising a coupling interface:
wherein the coupling interface is a planar annular flange extending axially away from the distal surface of the backing film.

18. The body side member of claim 1, wherein the channel comprises a pocket opening, and the pocket opening is located at a location that is radially closest to a center of the backing layer and axially closer to the distal surface of the backing film than to the proximal surface of the backing film.

19. The body side member of claim 1, wherein the channel comprises a first open end portion in communication with the pocket and a second closed end portion located in the first zone of the backing film.

20. The body side member of claim 4, wherein each individual and separate pocket of the plurality of individual and separate pockets is located in the second zone of the backing film.

21. The body side member of claim 1, comprising four individual pockets.

22. The body side member of claim 1, comprising six individual pockets.

23. The body side member of claim 20, wherein each individual and separate pocket is embedded in the backing film.

24. The body side member of claim 1, wherein the adhesive on the proximal surface of the backing film comprises a plurality of different adhesive materials provided in a side-by-side manner.

25. The body side member of claim 1, wherein the distal surface of the backing film comprises a first coupling interface for coupling the body side member to a stomal output collecting bag.

26. The body side member of claim 1, further comprising:
a stomal output collecting bag that is attachable to the distal surface of the backing film of the body side member.

27. The body side member of claim 1, further comprising:
a stomal output collecting bag including a second coupling interface;
wherein the second coupling interface is configured to couple with a first coupling interface connected to the body side member.

28. The body side member of claim 1, wherein the channel comprises a closed end portion that is configured to prevent fluid communication between the pocket and the stoma receiving opening.

29. The body side member of claim 1, wherein the channel comprises a closed end portion located in the first zone, and the cutting action removes the closed end portion to allow the moldable material to be dispensed from the pocket, through the channel, and into a custom-sized stoma receiving opening.

30. The body side member of claim 1, further comprising:
a second pocket formed between the proximal surface and the distal surface, with the second pocket separated from and independent from the pocket; and a second moldable material in the second pocket, where the second moldable material in the second pocket is different from the moldable material in the pocket.

\* \* \* \* \*

UNITED STATES PATENT AND TRADEMARK OFFICE
CERTIFICATE OF CORRECTION

| | | |
|---|---|---|
| PATENT NO. | : 11,033,418 B2 | Page 1 of 1 |
| APPLICATION NO. | : 15/766368 | |
| DATED | : June 15, 2021 | |
| INVENTOR(S) | : O'Brien et al. | |

It is certified that error appears in the above-identified patent and that said Letters Patent is hereby corrected as shown below:

In the Specification

In Column 9, Line 3, delete "is" and insert -- it --, therefor.

In Column 14, Line 39, delete "in" and insert -- is --, therefor.

In the Claims

In Column 14, Line 67, in Claim 1, delete "zone," and insert -- zone; --, therefor.

In Column 15, Line 24, in Claim 3, delete "pocket, and" and insert -- pocket; and --, therefor.

In Column 15, Line 30, in Claim 4, delete "furhter" and insert -- further --, therefor.

In Column 15, Line 37, in Claim 6, delete "any of claims" and insert -- claim --, therefor.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*